US00PP26231P2

(12) United States Plant Patent
Ubink

(10) Patent No.: US PP26,231 P2
(45) Date of Patent: Dec. 15, 2015

(54) ***ECHEVERIA* PLANT NAMED 'SAGITTA'**

(50) Latin Name: ***Echeveria agavoides*×*E. multicaulis***
Varietal Denomination: Sagitta

(71) Applicant: Gert Ubink, Kudelstaart (NL)

(72) Inventor: Gert Ubink, Kudelstaart (NL)

(73) Assignee: Handelskwekerij UBink B.V., Kudelstaart (NL)

( * ) Notice: Subject to any disclaimer, the term of this patent is extended or adjusted under 35 U.S.C. 154(b) by 85 days.

(21) Appl. No.: 13/998,399

(22) Filed: Oct. 29, 2013

(51) Int. Cl.
*A01H 5/00* (2006.01)

(52) U.S. Cl.
USPC ..... Plt./373

(58) Field of Classification Search
USPC ..... Plt./372, 373
See application file for complete search history.

*Primary Examiner* — Keith O. Robinson

(57) ABSTRACT

A new cultivar of *Echeveria* plant named 'Sagitta' that is characterized by narrow green leaves with a light green base, a grey-red tip, fine grey-red margins and yellow flowers.

2 Drawing Sheets

Botanical classification: *Echeveria agavoides*×*E. multicaulis.*

Variety denomination: 'Sagitta'.

BACKGROUND OF THE INVENTION

The present invention relates to a new and distinct cultivar of *Echeveria* plant botanically known as *Echeveria agavoides*×*E. multicaulis* and hereinafter referred to by the cultivar name 'Sagitta'.

'Sagitta' originated from the crossing of the female or seed parent an unnamed proprietary *Echeveria agavoides* cultivar and the male or pollen parent an unnamed proprietary *Echeveria multicaulis* cultivar. The crossing was conducted in 2006 in Kudelstaart, Netherlands. The resulting seeds were subsequently planted and grown. The cultivar 'Sagitta' was selected by the inventor in 2008 in a controlled environment as a single plant within the progeny of the stated cross in a cultivated area of Kudelstaart, Netherlands.

Asexual reproduction of the new cultivar 'Sagitta' first occurred by leaf cuttings in 2008 in Kudelstaart, Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Echeveria* cultivar 'Sagitta'. These traits in combination distinguish 'Sagitta' as a new and distinct cultivar apart from other existing varieties of *Echeveria* known by the inventor.

1. *Echeveria* 'Sagitta' exhibits green leaves with a light green base, grey-red tip and a fine grey-red margin.
2. *Echeveria* 'Sagitta' exhibits narrow leaves.
3. *Echeveria* 'Sagitta' exhibits yellow flowers.

The closest comparison cultivar is the co-pending application cultivar *Echeveria* 'Apus' (U.S. Plant patent application Ser. No. 13/998,400). 'Sagitta' is distinguishable from 'Apus' by the following characteristics:

1. *Echeveria* 'Sagitta' exhibits leaves that are thinner with a more pointed tip and are greener in color than the leaves of 'Apus'. In comparison, the leaves of 'Apus' are thicker with a more rounded tip and are greyer in color than the leaves of 'Sagitta'.

'Sagitta' is distinguishable from the female parent plant, an unnamed proprietary *Echeveria agavoides* cultivar, by the following characteristics:

1. *Echeveria* 'Sagitta' exhibits a larger number of leaves than the number of leaves of the female parent plant.
2. The leaves of 'Sagitta' are flatter than the leaves of the female parent plant. The leaves of the female parent plant are more curved than the leaves of 'Sagitta'.

'Sagitta' is distinguishable from the male parent plant parent plant, an unnamed proprietary *Echeveria multicaulis* cultivar, by the following characteristics:

1. *Echeveria* 'Sagitta' exhibits a more compact habit than the male parent plant.
2. The male parent plant has a more upright growth habit than the growth habit of 'Sagitta'.

BRIEF DESCRIPTION OF THE DRAWING

The accompanying photographs illustrate the distinguishing traits of *Echeveria* 'Sagitta'.

Figure 1:
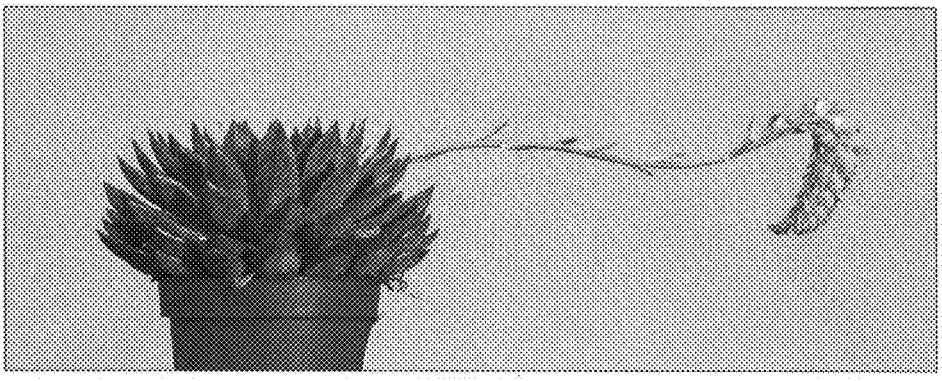
FIG. 1 shows an overall view of a 16 month old plant.
Figure 2:
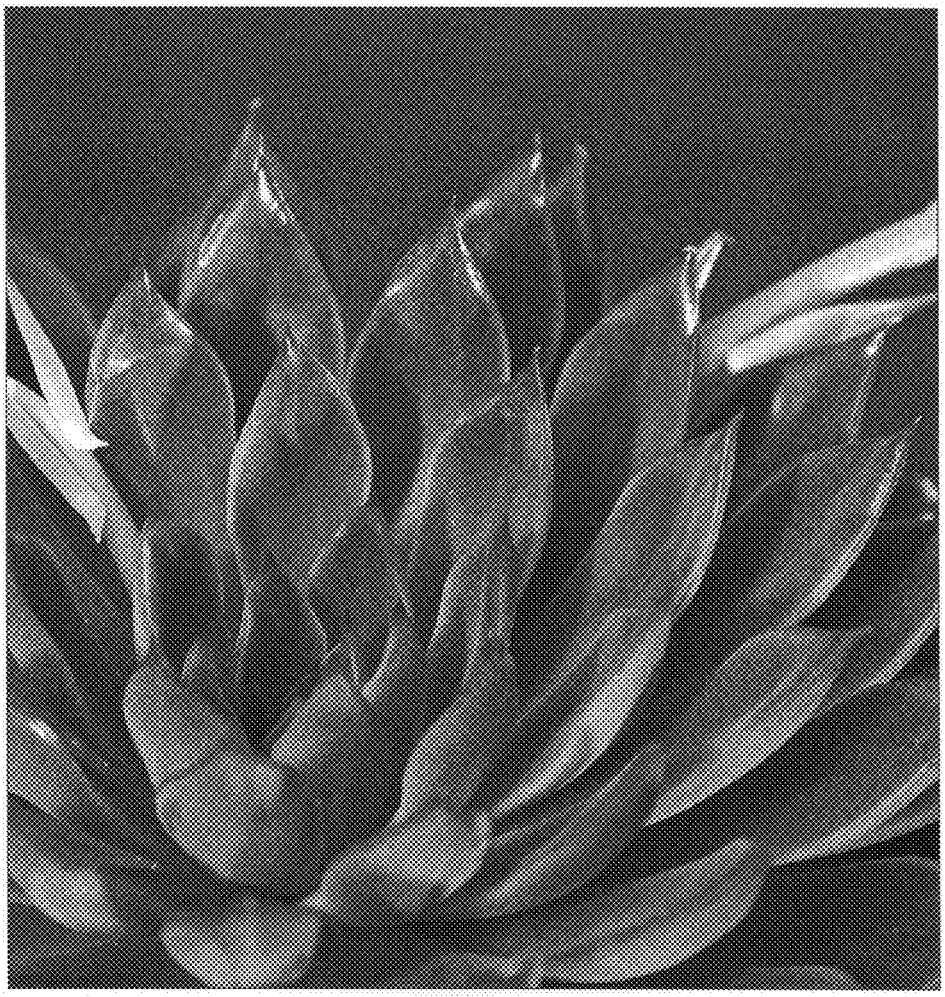
FIG. 2 shows an enlarged view of the leaves.
Figure 3:
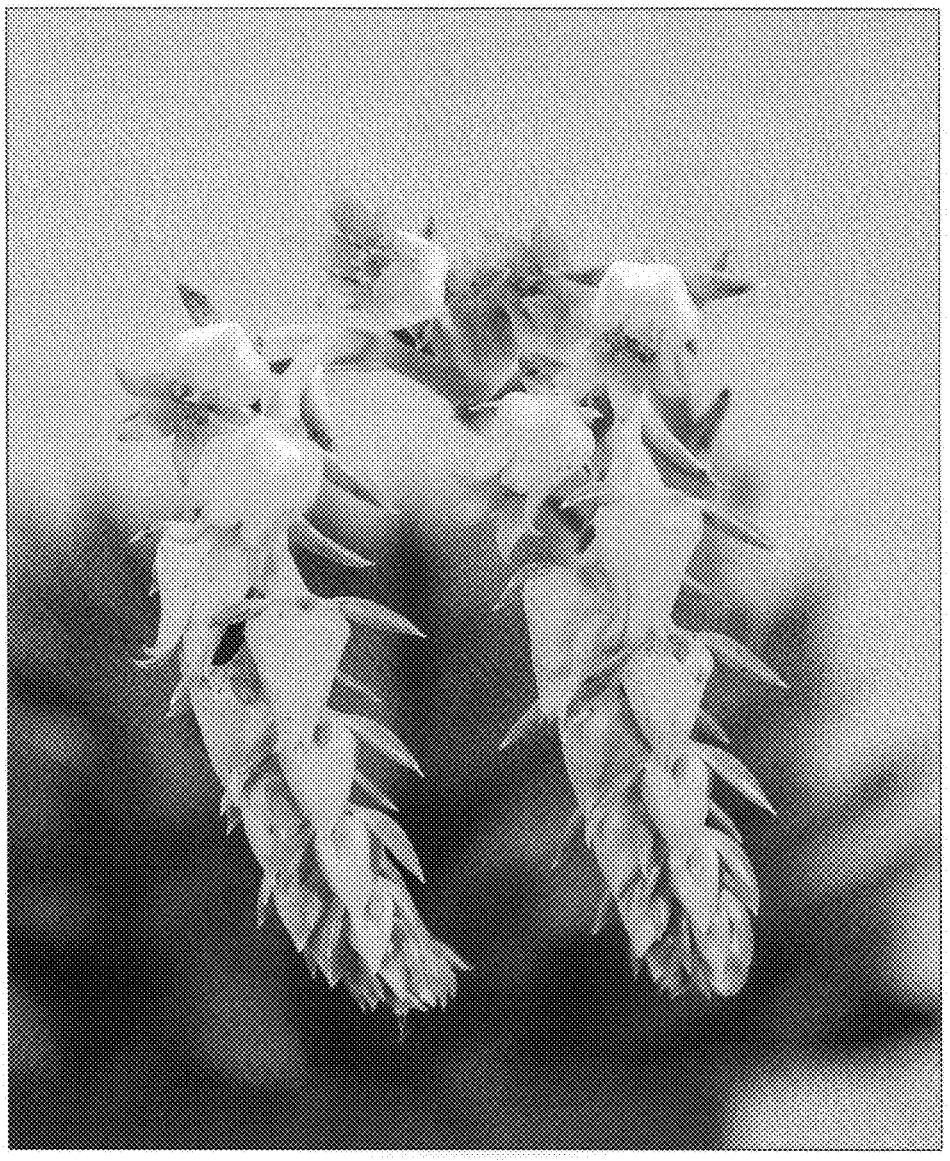
FIG. 3 shows an enlarged view of the flowers.

The photographs were taken using conventional techniques and although colors may appear different from actual colors due to light reflectance it is as accurate as possible by conventional photographic techniques.

BOTANICAL DESCRIPTION OF THE PLANT

The following is a detailed description of the new *Echeveria* cultivar named 'Sagitta'. Data was collected in Kudelstaart, Netherlands from 16 month old plants grown in a glass greenhouse in 10.5 cm. diameter containers. The time of year was Autumn and the temperature range was 18-25 degrees Centigrade during the day and 12-18 degrees Centigrade at night. The light level was natural light level. No photoperiodic treatments or growth retards were used. Color determinations are in accordance with The Royal Horticultural Society Colour Chart 2007 edition, except where general color terms of ordinary dictionary significance are used. The growing requirements are similar to the species. 'Sagitta' has not been tested under all possible conditions and phenotypic differences may be observed with variations in environmental, climatic, and cultural conditions, however, without any variance in genotype.

Botanical classification: *Echeveria agavoides*×*E. multicaulis* 'Sagitta'.

Annual or perennial: Perennial.

Parentage: 'Sagitta' is a hybrid of the female parent an unnamed proprietary *Echeveria agavoides* cultivar and the male parent an unnamed proprietary *Echeveria multicaulis* cultivar.

Plant type: Pot plant.

Plant shape: Basal rosette, non-branching.

Suitable container size: 7 cm. pots or larger.

Plant height: 7.5 cm.

Plant width: 15.9 cm.

Vigor: Moderate.

Low temperature tolerance: 10° Centigrade.

High temperature tolerance: 40° Centigrade.

Propagation: Leaf cuttings.

Time to initiate roots (summer): 14 days at 20° C.

Time to initiate roots (winter): 21 days at 20° C.

Time to produce a rooted cutting (summer): 120 days at 20° C.

Time to produce a rooted cutting (winter): 150 days at 20° C.

Growth rate: Approximately 1.8 cm. per month.

Crop time: Approximately 5 months.

Root system: Fibrous.

Root color: N155.

Foliage:

*Leaf arrangement*.—Basal rosette, non-branching.
*Compound or single*.—Single.
*Quantity of leaves per plant*.—Average 100.
*Leaf shape*.—Oblanceolate, slightly carinate.
*Leaf apex*.—Short apiculate.
*Leaf base*.—Broad cuneate. Leaf dimensions: 6.9 cm. in length and 1.8 cm. in width.
*Leaf thickness*.—0.5 cm.
*Texture*.—Glabrous both surfaces, succulent.
*Leaf aspect*.—Slightly cupped.
*Pubescence*.—Absent.
*Leaf margin*.—Entire.
*Venation pattern*.—None visible.
*Young leaf color* (*upper surface*).—138B, tip 184A.
*Young leaf color* (*lower surface*).—138B, tip 184A.
*Mature leaf color* (*upper surface*).—137B, base 143A, margins and tip 182A.
*Mature leaf color* (*lower surface*).—Varies from 137C to 191A, base 147D, margins and tip 182A.
*Leaf attachment*.—Sessile.

Flower:

*Flower arrangement*.—Compound raceme.
*Inflorescence dimensions*.—7.0 cm. in length and 5.3 cm. in width.
*Quantity of flowers per inflorescence*.—12.
*Quantity of flowers and buds per plant*.—Average 78.
*Natural flowering season*.—Continuous.
*Rate of flower opening*.—Lower flowers in raceme open first.
*Fragrance*.—Absent.
*Flower bud length*.—1.1 cm.
*Flower bud diameter*.—0.7 cm.
*Flower bud shape*.—Deltoid.
*Bud color*.—8B with tip 13A.
*Flower aspect*.—Outward to drooping.
*Flower shape*.—Campanulate.
*Flower dimensions*.—1.2 cm. in diameter and 1.2 cm. in height.
*Flower longevity*.—5 days.
*Number of petals*.—6.
*Fused or unfused*.—Base fused.
*Petal shape*.—Narrow ovate.
*Petal margin*.—Entire.
*Petal apex*.—Acute.
*Petal base*.—Fused.
*Petal texture*.—Glabrous both surfaces.
*Petal dimensions*.—1.2 cm. in length and 0.35 cm. in width.
*Petal color when opening* (*upper side*).—12A, base 4B.
*Petal color when opening* (*under side*).—12B, tip 13A.
*Petal color fully opened* (*upper side*).—12A, base 4B.
*Petal color fully opened* (*under side*).—12A, base 4B.
*Petal color fading to*.—11A, base 155B.
*Self-cleaning or persistent*.—Self-cleaning.

Sepals:

*Number of sepals*.—5.
*Sepal arrangement*.—Rotate.
*Sepal shape*.—Lanceolate.
*Sepal margin*.—Entire.
*Sepal apex*.—Acuminate.
*Sepal base*.—Cuneate.
*Sepal texture*.—Glabrous (both surfaces).
*Sepal dimensions*.—6.5 mm. in length and 2 mm. in width.
*Immature sepal color* (*inner side*).—137D.
*Immature sepal color* (*under side*).—137D.
*Mature sepal color* (*inner side*).—137C.
*Mature sepal color* (*under side*).—137D.

Calyx:

*Calyx dimensions*.—3 mm. in length and 12 mm. in diameter.

Scape:

*Scape dimensions*.—23.0 cm. in length and 4 mm. in diameter.
*Scape angle*.—20 degrees.
*Scape strength*.—Moderately strong.
*Scape texture*.—Smooth.
*Scape color*.—148D.

Peduncle:

*Peduncle dimensions*.—1.4 cm. in length and 2 mm. in diameter.
*Peduncle angle*.—40 degrees.
*Peduncle strength*.—Moderately strong.
*Peduncle texture*.—Smooth.
*Peduncle color*.—148D.

Pedicels:

*Pedicel dimensions*.—9 mm. in length and 1.5 mm. in diameter.
*Pedicel strength*.—Moderate.
*Pedicel texture*.—Smooth.
*Pedicel angle*.—40 degrees.
*Pedicel color*.—144B.

Reproduction organs:

*Stamen number*.—Average 12.
*Anther shape*.—Basifixed, narrow ovate.

*Anther length.*—1.0 mm.
*Anther color.*—148D.
*Filament length.*—5.0 mm.
*Filament color.*—12A.
*Amount of pollen.*—Moderate.
*Pollen color.*—157A.
*Pistil number.*—Average 5.
*Pistil length.*—3.0 mm.
*Stigma shape.*—Pointed.
*Stigma color.*—143A.
*Style length.*—2 mm.
*Style color.*—144B.
*Ovary color.*—157D.

Fruit and seed: Fruit and seed production has not been observed.

Disease and pest resistance: Disease and pest resistance has not been observed.

The invention claimed is:

1. A new and distinct variety of *Echeveria* plant named 'Sagitta' as described and illustrated.

* * * * *